United States Patent [19]

Wilkins

[11] 4,264,728

[45] Apr. 28, 1981

[54] INDIRECT MICROBIAL DETECTION

[75] Inventor: Judd R. Wilkins, Hampton, Va.

[73] Assignee: The United States of America as represented by the Administrator of the National Aeronautics and Space Administration, Washington, D.C.

[21] Appl. No.: 67,596

[22] Filed: Aug. 17, 1979

[51] Int. Cl.³ .......................... C12M 1/34; C12Q 1/70
[52] U.S. Cl. ........................ 435/5; 204/1 T; 204/195 B; 435/34; 435/291
[58] Field of Search .......... 23/230 B; 204/1 T, 195 P, 204/195 B; 210/96.2; 422/68; 435/29, 30, 34, 291, 817, 5

[56] References Cited

U.S. PATENT DOCUMENTS

| | | | |
|---|---|---|---|
| 3,403,081 | 9/1968 | Rohrback et al. | 435/291 |
| 3,506,544 | 4/1970 | Silverman | 435/14 |
| 3,743,581 | 7/1973 | Cady et al. | 435/291 |
| 3,868,223 | 2/1975 | Robock et al. | 204/195 B |
| 4,009,078 | 2/1977 | Wilkins et al | 435/873 |
| 4,020,830 | 5/1977 | Johnson et al. | 204/195 B |
| 4,051,006 | 9/1977 | Neti et al. | 204/1 T |
| 4,081,334 | 3/1978 | Suzuki et al. | 204/195 B |
| 4,129,478 | 12/1978 | Racine et al. | 435/4 |
| 4,172,770 | 10/1979 | Semersky et al. | 435/291 |
| 4,200,293 | 4/1980 | Wilkins et al. | 435/291 |

Primary Examiner—Peter A. Hruskoci
Attorney, Agent, or Firm—Wallace J. Nelson; John R. Manning; Howard J. Osborn

[57] ABSTRACT

The growth of microorganisms in a sample is detected and monitored by culturing microorganisms in a growth medium and detecting a change in potential between two electrodes separated from the microbial growth by a barrier which is permeable to charged particles but microorganism impermeable.

6 Claims, 8 Drawing Figures

INDIRECT MICROBIAL DETECTION

ORIGIN OF THE INVENTION

The invention described herein was made by an employee of the United States Government and may be manufactured or used by the Government for governmental purposes without the payment of any royalties thereon or therefor.

BACKGROUND OF THE INVENTION

The present invention relates to a method and apparatus for detecting and monitoring the growth of microorganisms which are shielded from the measuring device. The microbial growth is detected and monitored by measuring the difference in potential between two electrodes maintained in fluid or gaseous contact with the microorganisms, but kept from physical contact by a semipermeable barrier.

in microbiology, the indirect or remote detection of cell growth is desirable when conditions do not favor direct contact of the probe or sensor with the organisms or precludes physical manipulation of the cellular elements. Absence of contact between the microorganisms and the detecting device is especially advantageous when handling highly infectious organisms. Furthermore, direct contact between the sensor and the microorganisms could impede or alter the organisms' biochemical processes. The presence of the sensor in contact with the microorganisms would add a variable which would have to be considered in the interpretation of data. A measuring device which is in contact with microbial growth would have to be sterilized after each use. These are some of the handicaps which can be eliminated by using the indirect apparatus and method of detection of the present invention.

DESCRIPTION OF THE PRIOR ART

A number of indirect methods are available for monitoring the growth of microorganisms. For example, a microcalorimetric method measures the amount of heat generated during cell growth wherein the amount and types of gases evolved during metabolism can be measured with gas chromatographs. A radiometric technique has also been employed which measures tagged $CO_2$ evolved from the cellular breakdown of tagged $C_{14}$ glucose. Each of these techniques requires sophisticated instrumentation and highly trained operators. Optical methods have been employed which measure absorbed or reflected light thereby providing an indication of cell mass. The problem with this technique is that it fails to differentiate between live and dead cells. Total gas pressure for gas producing microorganisms can be measured with pressure transducers but this requires a gas tight system.

A direct method for electroanalytical detection of microorganisms was disclosed by Wilkins et al, U.S. Pat. No. 4,009,078. In this system, the microorganisms to be tested gradually concentrate about a measuring electrode and the electrostatic charge of the organisms at the measuring electrode creates a difference in potential relative to an isolated reference electrode. For the device to function, it is essential that contact be maintained between the microorganisms and the measuring electrode. If the measuring electrode loses contact with the microorganisms, the potential difference is eliminated. As a consequence, it is impossible to operate the device without contaminating the measuring electrode, without distinguishing between the measuring electrode and a reference electrode, and, generally, without encountering all of the difficulties that are inherent in any direct method of detecting microbial growth in which there is contact between the microorganisms and the measuring device.

SUMMARY OF THE INVENTION

It is thus seen that there is a definite need in the art for an improved, indirect microorganism detection and growth monitoring system.

Accordingly, one object of the present invention is to provide an indirect method for the detection of microbial growth in which there is no contamination of the sensing device.

Another object of the invention is to provide an indirect method for the electroanalytical monitoring of microbial growth, wherein the monitoring electrodes are shielded from the microorganisms.

Yet another object of the invention is to provide an indirect method for the electroanalytical monitoring of the growth of highly infectious organisms that reduces the danger of contamination.

Still another object of the present invention is to provide an indirect method for the electroanalytical monitoring of microbial growth wherein the measuring electrodes do not influence or interfere with the biochemical processes of the microorganisms.

A further object of the present invention is to provide a sensor for monitoring microbial growth that can be repeatedly used without requiring sterilization.

Another object of the present invention is to provide an indirect method for the electroanalytical monitoring of microbial growth on agar surfaces.

Yet another object of the present invention is to provide a sensor for the detection and monitoring of substances affecting microbial growth, such as enzymes, toxins, viruses, and water and air pollutants.

BRIEF DESCRIPTION OF THE DRAWINGS

These and other objects of the invention are attained by the present invention by separating two electrodes from a sample of microbial growth by means of a semipermeable barrier that prevents the flow of microorganisms and monitoring the change in potential between the electrodes. The growing organisms produce charged particles which create the difference in potential.

A more complete appreciation of the invention and many of the attendant advantages thereof will be better understood as the same becomes more apparent by reference to the following detailed description when considered in connection with the accompanying drawings, wherein.

DETAILED DESCRIPTION OF THE INVENTION

Figure 1:
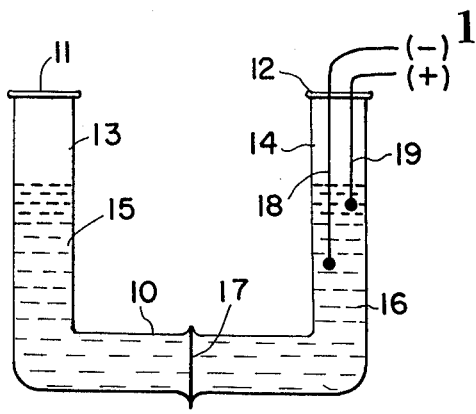
FIG. 1 illustrates the preferred embodiment of the electroanalytical measuring device of the present invention.

Referring now to the drawings, and more particularly to FIG. 1, there is shown an embodiment of a parabiotic vessel 10 with two chambers 13 and 14 sealed by self-sealing resilient caps 11 and 12. Platinum electrodes 18 and 19 extend through resilient cap 12 into chamber 14 and contact a solution of sterile growth medium 16. It is not necessary to distinguish between a measuring electrode and a reference electrode because the presence of microorganisms will be manifested if there is merely a relative difference in potential between two electrodes. As a consequence, in this preferred embodiment of the present invention, both electrodes are made of the same material. Platinum demonstrates qualities of conductivity which render that element particularly suitable as an electrode for the purposes of the present invention. Other materials, for example, gold, palladium and stainless steel, can also function as electrodes. If the same material is used for both electrodes the direction of the response curve can be controlled by increasing the surface area of one electrode relative to the surface area of the second electrode. In the illustrated embodiment, the surface area of electrode 18 in contact with the growth medium 16 is four times greater than the surface area of electrode 19 in contact with the growth medium. Growth medium 15 of chamber 13 is inoculated with a sample of microorganisms to be analyzed. The microorganisms may be cultured in any suitable growth medium, such as brain-heart infusion, trypticase soy broth (TSB) trypticase soy broth +$CO_2$, phenol red broth base +1% glucose, litmus milk, and the like.

The growth media and test conditions can be chosen so as to selectively encourage or inhibit the growth of particular microorganisms and some of the types of bacteria whose growth has been experimentally monitored are: *Escherichia coli, Enterobactor aerogenes, Citrobacter intermedium, Citrobacter freundii, Serratia marcescens, Pseudomonas aeruginosa, Klebsiella pneumoniae, Alcaligenes faecalis, Proteus mirabilis, Staphylococcus aureus, Staphylococcus epidermidis, Streptococcus faecalis, Streptococcus pyogenes,* and *Scarcina lutea*.

A semipermeable membrane 17 separates chambers 13 and 14 and shields the growth medium 16 of chamber 14 from contact with the microorganisms growing in chamber 13. Charged particle flow across the semipermeable membrane 17 is uninterrupted. The material that shields the electrodes from contact with the microorganisms may be made of any substance which permits the flow of charged particles but which does not permit the movement of microorganisms. Membranes which are impermeable to microorganisms, such as cellulose acetate membranes, ceramic or porous plastic films with a porosity of 0.10 to 0.45 $\mu$m, are suitable and are commercially available, for example, from the Millipore Corporation, Bedford, Massachusetts. Electrodes 18 and 19 are connected to the appropriate terminals of a potentiometer with an input impedance of at least one megohm and the changing potential between electrodes 18 and 19 is graphically monitored and recorded by a strip chart recorder as further explained hereinafter in reference to FIG. 2.

Figure 2:
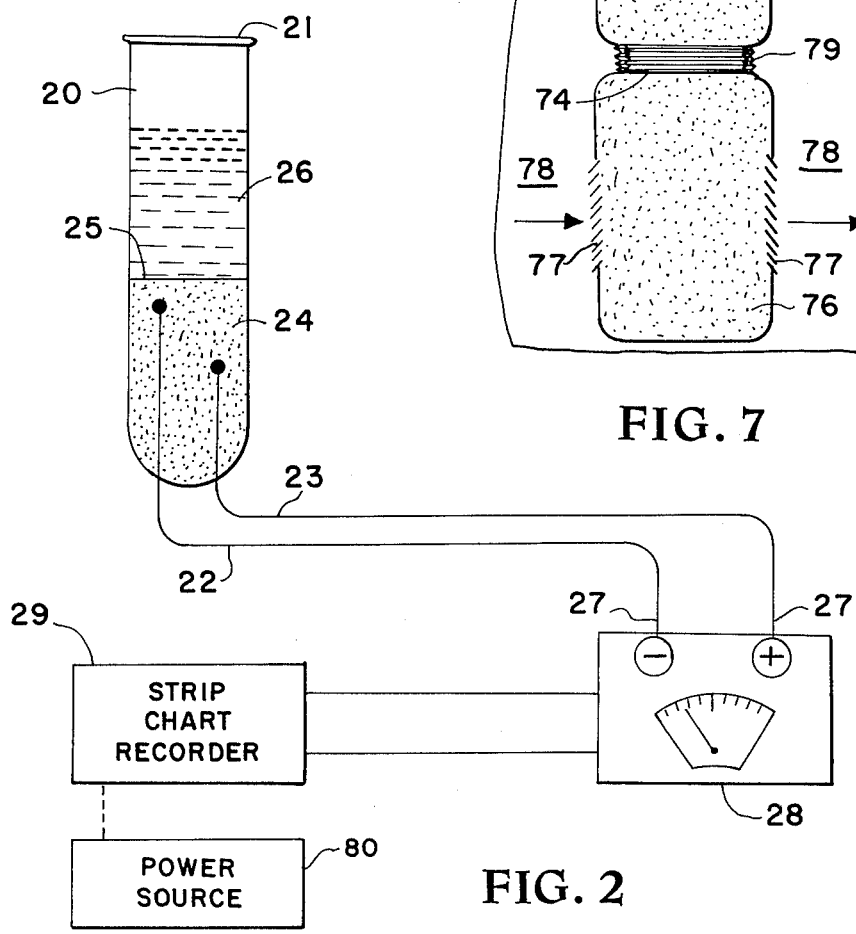
FIG. 2 illustrates another embodiment of an electroanalytical measuring device according to the present invention.

Referring now more particularly to the embodiment illustrated in FIG. 2, a single chamber 20 is sealed by a resilient cap 21. The bottom portion of the chamber contains a semipermeable substance 24 which will not support microbial growth. The electrodes in this embodiment are shielded from the microorganisms by the use of a gel, such as agar gel. Gelatin, dextran gel, carrageenan gels, acrylamide, and the like, may all be used to shield the electrodes as long as the microorganisms are not viable in the gel. A gel shielding may be particularly suitable if the effect of a bacteriophage sample on microbial growth is to be analyzed, because the virus may be able to penetrate a semipermeable membrane. Two platinum electrodes 22 and 23 extend and are sealed through openings (not shown) in the bottom of chamber 20. In the illustrated embodiment, electrode 22 contacts four times more surface area of the shielding substance 24 than electrode 23. A growth medium 26 containing a sample of the microorganism to be analyzed is positioned on the surface 25 of shielding substance 24. Leads 27 from the electrodes 22 and 23 are connected to the appropriate terminals of a potentiometer 28 with an impedance of at least one megohm from power supply 80 and a difference in potential between the electrodes is measured and recorded by a strip chart recorder 29.

Figure 3:
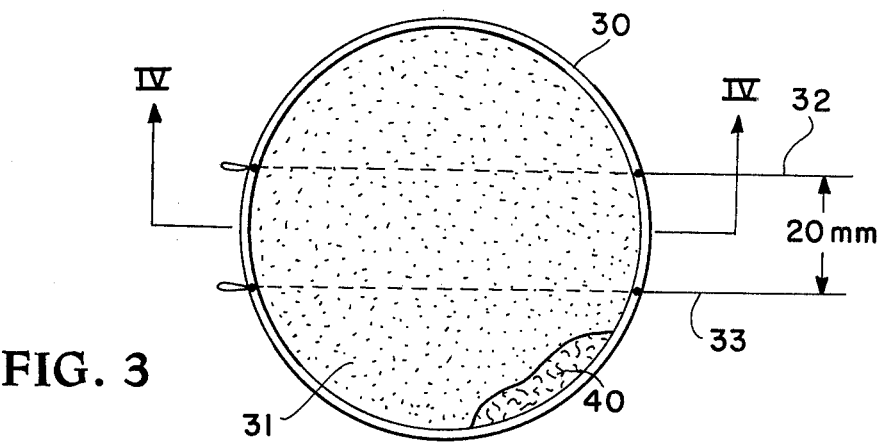
FIG. 3 is a top view of another embodiment of an electroanalytical measuring device according to the present invention.
Figure 4:
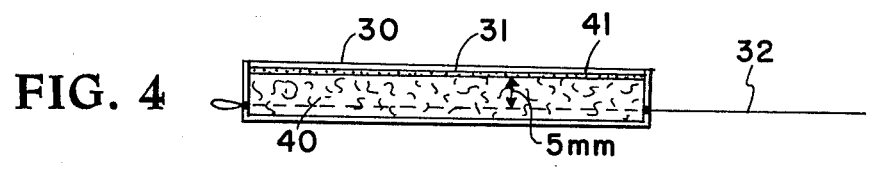
FIG. 4 depicts a schematic cross-section of the measuring device taken along line IV—IV of FIG. 3.

Referring now to FIGS. 3 and 4, an embodiment of the present invention wherein a non-nutrient agar gel is employed to shield the electrodes is shown. Leads from a one megohm potentiometer (as in FIG. 2) are connected to platinum wire electrodes 32 and 33 at one side of a petri dish 30. The electrodes extend through openings (not shown) in the petri dish 30, and emerge through the opposite side of the petri dish, where they are folded back to the side of the dish. The distance between electrodes 32 and 33 in this embodiment is 20 mm and 60 mm of sterile non-nutrient 1.0% agar 40 completely covers the electrodes 32 and 33. The distance from the electrodes to the surface of the agar is 5.0 mm. Microorganisms are cultured in a 0.5% agar mixture and a sample of the microorganism-agar mixture is spread on the surface 41 of the 1.0% non-nutrient agar 40 contained in the petri dish 30. The microorganism-agar mixture immediately solidifies to form a growth layer 31 shielded from contact with platinum electrodes 32 and 33 by the 1.0% agar gel which does not support microbial growth. The agar gel, however, does not inhibit the passage of charged particles. A difference in potential between the electrodes is measured by the potentiometer.

Figure 5:
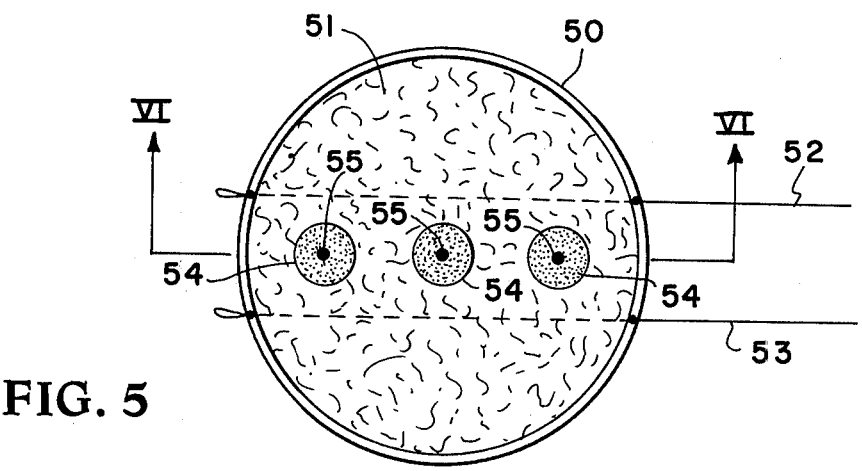
FIG. 5 is another embodiment of the measuring device similar to FIG. 3 wherein the microorganisms are grown in pockets located between shielded electrodes.
Figure 6:
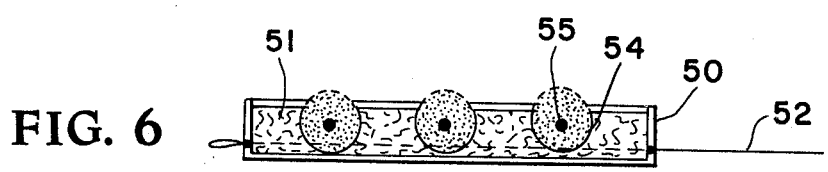
FIG. 6 depicts a schematic cross-section of the measuring device taken along line VI—VI of FIG. 5.

Another embodiment of the present invention using non-nutrient agar as a shield is illustrated in FIGS. 5 and 6. As shown therein, two platinum electrodes 52 and 53 pass through suitable openings and extend along the bottom of petri dish 50. The electrodes emerge through suitable openings (not shown) in the dish and are folded back to the side of petri dish 50. In this embodiment, petri dish 50 is filled with 60 ml of a non-nutrient 1.0% agar gel 51. Three 12.5 mm wells 54 are cut out of the 1.0% agar using a sterile cork borer. The wells are located between electrodes 52 and 53 and the distance, in this illustrated embodiment, from the edge of each well to the electrodes is 3.5 mm. The microorganisms to be analyzed are cultured in a growth medium containing melted 0.5% agar. Samples of the microorganism-agar mixture are added to each well with the agar solidifying on contact to form pockets of microbial growth 55. Electrodes 52 and 53 are connected to a one megohm potentiometer (as in FIG. 2) which measures a difference in potential between the two electrodes.

Figure 7:
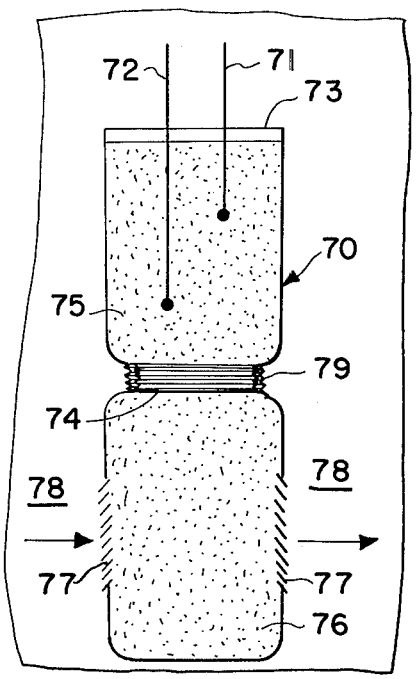
FIG. 7 illustrates an embodiment of the present invention useful to detect the presence of growth-affecting substances.

FIG. 7 shows an embodiment of the present invention useful for the detection of substances that influence microbial growth. Platinum electrodes 71 and 72 extend through closure 73 into chamber 75 of the detecting device 70. Chambers 75 and 76 contain sterile growth medium and are separated by semipermeable membrane 74. Chamber 76 is detachable and, in this embodiment, is connected to detecting device 70 by means of a threaded joint 79. As shown, semipermeable membrane 74 is affixed to chamber 75, although the device would function as well if the membrane were affixed to chamber 76. Microorganisms are added to chamber 76 and their growth is monitored by recording the changing difference in potential between electrodes 71 and 72. Chamber 76 is immersed in liquid sample 78, an environment containing substances which influence microbial growth. Liquid environment 78 is heated in a conventional manner to ensure proper incubation of the microbial growth. Semipermeable membranes 77, positioned in the form of windows on opposite sides of chamber 76, permit contact of the microbial growth to the external environment 78. The presence of any substance in the external environment which influences microbial growth is detected by monitoring a change in the microbial growth rate. The presence, quantity and antibacterial qualities of bacteriophages, toxins and water pollutants may be determined with this embodiment of the invention. The detection device functions as a one-shot probe that gives a single all-or-none response. It also works to provide an approximate quantitative indication over a period of time of the presence of a particular substance.

Although fluid contact between chambers 75 and 76 must be maintained across semipermeable membrane 74 while measuring the change in microbial growth rate, after the measurement, culture chamber 76 is detached from the electrode containing chamber 75. Since the electrodes 71 and 72 are not contaminated, a new culture chamber can be attached to chamber 75 quickly and easily. The semipermeable membrane 74 of chamber 75 must be sterilized with ultraviolet light or a similar agent before commencing a new measurement.

The specific quantities and size limitations included in the foregoing description and drawings are to merely provide illustrations of the invention and are not intended to limit the applicability of the invention.

It is thus seen that each embodiment of the present invention is based upon the discovery that growing organisms create an electrostatic-like potential which results in the accumulation of charged particles. These charged particles are capable of flowing across barriers, or through substances, which do not permit the flow of microorganisms. Once the charged particles traverse such a semipermable barrier, their presence can be detected as a potential difference between two electrodes. The detection of a potential difference indicates the presence of a colony of microorganisms; monitoring the change in the potential difference provides an indication of the rate of microbial growth.

If the microorganism to be tested is a member of the gram-negative group, known for the ability to produce hydrogen, then the charge can be explained as the consequence of a reaction at the surface of the electrodes. In the course of growth, molecular hydrogen, $H_2$, is produced and migrates across the semipermeable barrier. The molecular hydrogen, in equilibrium with the hydrogen ion in the presence of platinum, liberates two electrons, as shown in the following equation:

$$H_2 \xrightarrow{Pt} 2H^+ + 2e^-.$$

A similar response, although not as pronounced, is obtained with gram-positive, or non-hydrogen producing, microorganisms. The source of the charge created by the gram-positive group is unknown at this time. It is possible that, in the course of cell division, all microorganisms emit an "electrostatic like" charge. The gram-negative group, consequently, may be emitting a charge substantially the same as the charge emitted by the gram-positive group, the only difference being that the charge that results from release of molecular hydrogen, in the case of the gram-negative bacteria, becomes superimposed on the response indicating the "electrostatic like" charge characteristic of all organisms.

Because of the relatively weak, electrostatic like potential difference existing between the electrodes, it is necessary to use a potentiometer with an impedance of at least one megohm. Other electrical apparatus, such as amplifiers or signal devices, or a multichannel setup, can be included.

Because the electrodes are never contaminated and, consequently, do not require sterilization once in use, the unit of the device containing the electrodes can be permanently set in place, either in the laboratory or in a field test situation, e.g., in a natural waterway near a factory or sewage treatment outlet. The unit of the device which contains the microbial growth, on the other hand, can be made to be easily disposable.

The microbial growth can also be incubated or agitated to increase cell growth as conventional in the art. There is a linear relationship between inoculum size and detection time with a minimum microbial concentration of from $10^5$ to $10^6$/ml required for a response.

Figure 8:
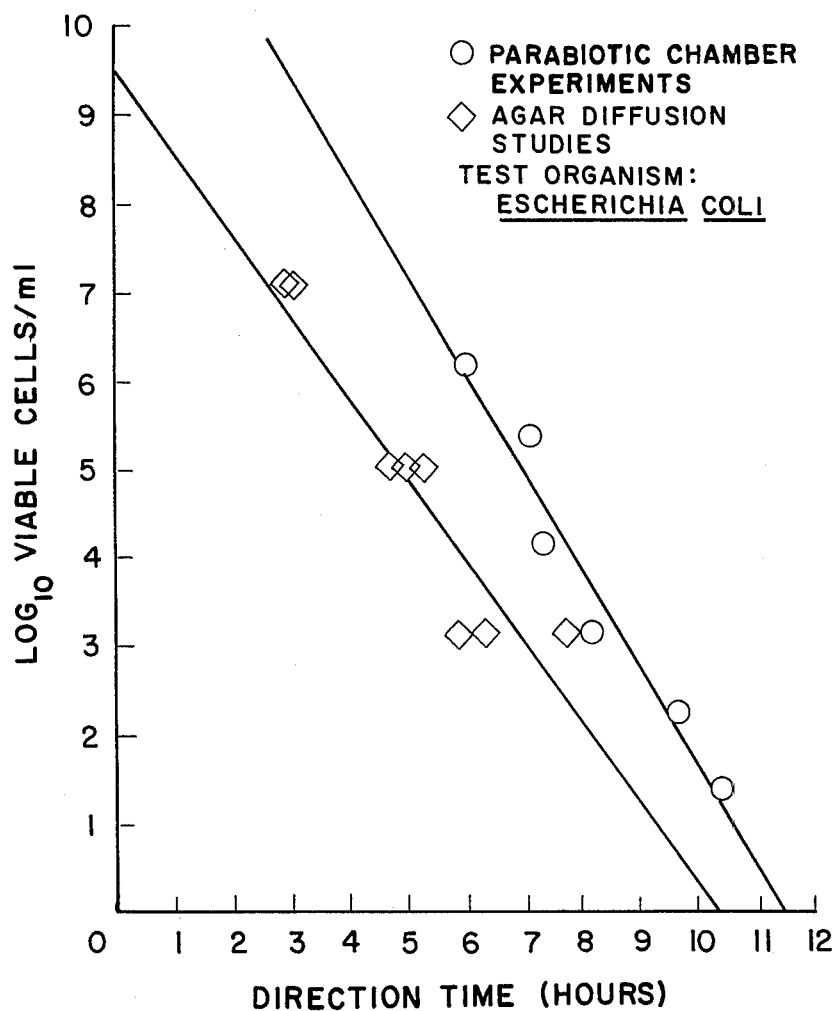
FIG. 8 shows a graph depicting the relationship between the inoculum size of a specific microorganism, *Escherichia coli*, and the length of detection time.

FIG. 8 shows a graph of the relationship between inoculum size and the length of detection time for *Escherichia coli*. Similar relationships are observed with other types of microbial growth. The temperature range of the test conditions can vary between 15° and 60° C. and pressure is not a factor. The present invention is thus useful to monitor the growth of any type of microorganisms, such as yeasts, fungi or bacteria. For both hydrogen producing and nonhydrogen producing microorganisms, the typical response consists of an initial lag period followed by a sharp increase in voltage, followed by a period of decline.

Although the invention has been described with reference to exemplary embodiments thereof, it will be understood that variations and modifications can be effected in these embodiments without departing from the scope and spirit of the invention.

What is claimed is:

1. An indirect method for detecting substances which influence microbial growth, which comprises:
 separating a growth medium suitable for microorganisms into two compartments by a first semipermeable membrane barrier that is impermeable to microorganisms;

providing at least one additional semipermeable membrane barrier in one of the compartments and inoculating this compartment with microorganisms;

placing two electrodes in the other of the two compartments;

maintaining said electrodes in fluid or gaseous contact with said microorganisms;

bringing the compartment containing microbial growth into contact with an environment containing at least one substance that influences microbial growth and is permeable to the one additional semipermeable membrane; and detecting and monitoring the change in potential between the two electrodes with a potentiometer having an impedance equal to at least one megohm to detect the substance which influences microbial growth in said environment.

2. The method of claim 1 wherein the environment substance influencing growth is selected from the group consisting of toxins, bacteriophages and water pollutants.

3. Apparatus for indirectly detecting and measuring microbial growth comprising:

a container;

a first chamber in said container housing a microbial growth medium and containing microorganisms said first chamber being provided with at least one semipermeable membrane in a sidewall thereof to permit microorganism growth influencing environment to contact the microbial growth medium;

a second chamber in said container housing a microbial growth medium;

a semipermeable membrane barrier impermeable to said microorganisms disposed between and maintaining said first and second chambers separate;

a pair of electrodes disposed in said second chamber and embedded in the said microbial growth medium;

an electric circuit connected to said pair of electrodes;

detecting means connected to said electric circuit to detect changes in electrical potential between said pair of electrodes;

said detecting means being a potentiometer with an impedance equal to at least one megohm;

whereby, microbial growth in said first chamber will produce charged particles that permeate said semipermeable barrier to contact said pair of electrodes and cause a change in electrical potential therebetween that is detected by said detecting means.

4. The apparatus of claim 3 wherein said potentiometer is connected to a strip chart recorder that permanently records the changes in electrical potential between said electrodes.

5. The apparatus of claim 3 wherein said microbial growth medium is selected from the group consisting of: brain-heart infusion, trypticase soy broth (TSB), trypticase soy broth $+CO_2$, phenol red broth base $+1\%$ glucose, and litmus milk.

6. The apparatus of claim 3 wherein said first and said second chambers are provided with a separable threaded joint connection.

* * * * *